US010863898B2

(12) United States Patent
Carrafa et al.

(10) Patent No.: US 10,863,898 B2
(45) Date of Patent: Dec. 15, 2020

(54) SYSTEM AND METHOD FOR DETERMINING DISTANCES FROM AN OBJECT

(71) Applicant: JAND, INC., New York, NY (US)

(72) Inventors: Joseph Carrafa, Brooklyn, NY (US); Molly Rhodes, New York, NY (US)

(73) Assignee: JAND, Inc., New York, NY (US)

( * ) Notice: Subject to any disclaimer, the term of this patent is extended or adjusted under 35 U.S.C. 154(b) by 194 days.

(21) Appl. No.: 16/282,813

(22) Filed: Feb. 22, 2019

(65) Prior Publication Data

US 2019/0183331 A1    Jun. 20, 2019

Related U.S. Application Data

(63) Continuation of application No. 15/351,676, filed on Nov. 15, 2016, now Pat. No. 10,251,545, which is a continuation of application No. 14/732,435, filed on Jun. 5, 2015, now Pat. No. 9,532,709.

(51) Int. Cl.
| | |
|---|---|
| *A61B 3/00* | (2006.01) |
| *A61B 3/032* | (2006.01) |
| *G06T 7/80* | (2017.01) |
| *G01C 3/08* | (2006.01) |

(52) U.S. Cl.
CPC ............ *A61B 3/032* (2013.01); *A61B 3/0025* (2013.01); *A61B 3/0041* (2013.01); *A61B 3/0058* (2013.01); *G01C 3/08* (2013.01); *G06T 7/80* (2017.01); *G06T 2200/24* (2013.01); *G06T 2207/30201* (2013.01); *G06T 2207/30204* (2013.01)

(58) Field of Classification Search
CPC ..... A61B 3/0025; A61B 3/005; A61B 3/0041; A61B 3/0033; A61B 3/0058
USPC ................................. 351/223, 222, 237, 246
See application file for complete search history.

(56) References Cited

U.S. PATENT DOCUMENTS

| | | |
|---|---|---|
| 5,877,841 A | 3/1999 | Jeon |
| 5,946,075 A | 8/1999 | Horn |
| 6,238,049 B1 | 5/2001 | Griffin et al. |
| 6,386,707 B1 | 5/2002 | Pellicano |
| 6,556,131 B1 | 4/2003 | Besharat et al. |

(Continued)

FOREIGN PATENT DOCUMENTS

| | | |
|---|---|---|
| WO | 2013126989 A1 | 9/2013 |
| WO | 2014064719 A1 | 5/2014 |

(Continued)

OTHER PUBLICATIONS

Extended Search Report for EP 16804442.8, dated Mar. 18, 2019, 9 pages.

(Continued)

*Primary Examiner* — Hung X Dang
(74) *Attorney, Agent, or Firm* — Duane Morris LLP

(57) ABSTRACT

A process for assessing at least one characteristic of a user's vision includes determining a characteristic of at least one camera of a mobile device; using the at least one camera, capturing at least one image of an object; determining, with reference to a portion of the at least one image composed of the object, a distance from the mobile device to the object at a time of capture of the at least one image; and receiving input from the user in response to material presented on the object.

20 Claims, 13 Drawing Sheets

(56) References Cited

U.S. PATENT DOCUMENTS

| | | |
|---|---|---|
| 6,578,966 B2 | 6/2003 | Fink et al. |
| 7,222,091 B2 | 5/2007 | Yoshida |
| 7,267,439 B2 | 9/2007 | Toshima et al. |
| 7,367,675 B2 | 5/2008 | Maddalena et al. |
| 7,374,285 B2 | 5/2008 | Toshima et al. |
| 7,415,212 B2 | 8/2008 | Matsushita et al. |
| 7,429,109 B2 | 9/2008 | Toshima et al. |
| 7,819,524 B2 | 10/2010 | Kanazawa et al. |
| 8,066,376 B2 | 11/2011 | Wang et al. |
| 8,083,353 B2 | 12/2011 | Hytowitz |
| 8,322,857 B2 | 12/2012 | Barbur et al. |
| 8,740,386 B2 | 6/2014 | Foster |
| 8,757,805 B2 | 6/2014 | Hytowitz |
| 8,783,871 B2 | 7/2014 | Pamplona et al. |
| 8,786,707 B1 | 7/2014 | Ettinger |
| 9,033,508 B2 | 5/2015 | Bartlett et al. |
| 9,055,904 B2 | 6/2015 | Yoo et al. |
| 9,066,683 B2 | 6/2015 | Zhou |
| 9,230,062 B2 | 1/2016 | Seriani |
| 9,236,024 B2 | 1/2016 | Coon |
| 9,237,842 B2 | 1/2016 | Lee et al. |
| 9,237,846 B2 | 1/2016 | Mowrey et al. |
| 9,314,154 B2 | 4/2016 | Palanker et al. |
| 9,532,709 B2 | 1/2017 | Carrafa |
| 9,549,669 B2 | 1/2017 | Limon |
| 2008/0189173 A1 | 8/2008 | Bakar et al. |
| 2008/0309879 A1* | 12/2008 | Hirji .................. A61B 3/032 351/223 |
| 2012/0050686 A1 | 3/2012 | Bartlett et al. |
| 2012/0069179 A1 | 3/2012 | Gish |
| 2012/0069199 A1 | 3/2012 | Chang et al. |
| 2012/0212706 A1 | 8/2012 | Chou et al. |
| 2012/0327123 A1 | 12/2012 | Felt |
| 2013/0026217 A1 | 1/2013 | Boudville |
| 2013/0169801 A1 | 7/2013 | Martin et al. |
| 2013/0271478 A1 | 10/2013 | Lazzaro et al. |
| 2014/0268060 A1 | 9/2014 | Lee et al. |
| 2014/0293228 A1 | 10/2014 | Hytowitz |
| 2015/0070650 A1 | 3/2015 | Seriani |
| 2015/0098060 A1 | 4/2015 | Zhou |
| 2015/0164318 A1 | 6/2015 | Zhou |
| 2016/0035122 A1 | 2/2016 | Stewart et al. |
| 2016/0086780 A1 | 3/2016 | Pamplona et al. |
| 2016/0098528 A1 | 4/2016 | Seriani |
| 2016/0128560 A1 | 5/2016 | Lee et al. |
| 2016/0128567 A1 | 5/2016 | Lee et al. |
| 2016/0157711 A1 | 6/2016 | Maddalena et al. |
| 2016/0157716 A1 | 6/2016 | Pamplona et al. |
| 2017/0079523 A1 | 3/2017 | Limon |

FOREIGN PATENT DOCUMENTS

| | | |
|---|---|---|
| WO | 20140195951 A1 | 12/2014 |
| WO | 2015148442 A1 | 10/2015 |
| WO | WO 2015/19714 A1 | 12/2015 |
| WO | 2016046186 A1 | 3/2016 |
| WO | 2016084086 A1 | 6/2016 |
| WO | 2016181308 A1 | 11/2016 |
| WO | 2016181309 A1 | 11/2016 |
| WO | 2016181310 A1 | 11/2016 |

OTHER PUBLICATIONS

International Search Report and the Written Opinion of the International Searching Authority from corresponding PCT/US16/35532, dated Jun. 2, 2016.

Zhang, "A Flexible New Technique for Camera Calibration," IEE Transactions on Pattern Analysis and Machine Intellingence, 22(11)1330-1334, 2000.

Non-Final Office Action for U.S. Appl. No. 15/351,676, dated Jul. 9, 2018, 7 pages.

Australian Examination Report No. 1 for Application No. 2016270934, dated Feb. 19, 2018, 3 pages.

Sep. 10, 2020 Office Action from Canadian Patent Application No. 3,011,428.

* cited by examiner

SYSTEM AND METHOD FOR DETERMINING DISTANCES FROM AN OBJECT

CROSS REFERENCE TO RELATED APPLICATIONS

This application claims the benefit under 35 U.S.C. § 120 as a continuation of U.S. application Ser. No. 15/351,676, filed Nov. 15, 2016, now U.S. Pat. No. 10,251,545, and titled "SYSTEM AND METHOD FOR DETERMINING DISTANCES FROM AN OBJECT," which is a continuation of U.S. application Ser. No. 14/732,435, filed Jun. 5, 2015, now U.S. Pat. No. 9,532,709, and titled "SYSTEM AND METHOD FOR DETERMINING DISTANCES FROM AN OBJECT," each of which is incorporated herein by reference in its entirety.

BACKGROUND

Technical Field

The technical field generally relates to camera calibration and distance determination, and more particularly, in one aspect, to systems and methods for calculating user distance from an object during an eye examination.

Background Discussion

Eye examinations are routinely used to determine the appropriate lens prescription for patients. One variable that must be known to perform an effective eye exam is the distance between a test subject and the displayed eye test. Eye exams have traditionally been performed by optometrists or the like in an office where a set distance from the patient to an eye chart or other testing material is easily maintained. Efforts to translate eye exam procedures from a doctor or technician's office to non-traditional locations such as self-administered tests at home are hampered by the difficulties associated with a user's ability to determine with confidence his or her distance from the testing material so that reliable results may be obtained. Proposed solutions such as using measuring tape or counting steps to determine a distance from a computer screen displaying an eye test require additional equipment or steps and may erode a user's confidence in the results, making a test administered out of office less attractive.

SUMMARY

According to one aspect, a process for assessing at least one characteristic of a user's vision is provided. The process includes determining a characteristic of at least one camera of a mobile device; using the at least one camera, capturing at least one image of an object; determining, with reference to a portion of the at least one image composed of the object, a distance from the mobile device to the object at a time of capture of the at least one image; and receiving input from the user in response to material presented on the object. According to one embodiment, the object is a display screen of a second device, and receiving input from the user includes receiving input at one of the mobile device and the second device.

According to another embodiment, the process includes guiding a user to a location relative to the object for conducting an assessment of the user's vision. According to a further embodiment, guiding the user includes providing an instruction to the mobile device to display an indication of a current distance between the mobile device and the object. According to a still further embodiment, the process includes providing an indication from the mobile device to the user when the location has been reached. According to yet a further embodiment, the process includes, responsive to receiving the input from the user in response to material presented on the object, guiding the user to a second location relative to the object.

According to another embodiment, the object is a display screen, and guiding the user includes providing an instruction to the user to move in a direction relative to the display screen. According to a further embodiment, the instruction to the user is provided by at least one of the mobile device and the display screen.

According to another embodiment, the object is a display screen of a second device, and the process includes pairing the mobile device to the second device. According to a further embodiment, pairing includes receiving input entered on the mobile device indicative of an identifier displayed on the display screen. According to a still further embodiment, the input includes a token comprising at least one of an email address or code.

According to another embodiment, the process includes determining, from the input from the user, an adjustment to at least one aspect of the user's current corrective lens prescription.

According to another aspect, a process for operating a rangemeter is provided. The process includes capturing, using at least one camera of a mobile device, a plurality of images of a calibration pattern from a plurality of angles; using the mobile device, determining a current distance from the mobile device to an object; and using the mobile device, guiding a user to a specified distance from the object. According to one embodiment, the process includes determining, from the plurality of images, at least one characteristic of the at least one camera.

According to another embodiment, the object is a display screen, and guiding the user includes providing an instruction to the user to move in a direction relative to the display screen. According to a further embodiment, the instruction to the user is provided by at least one of the mobile device and the display screen.

According to yet another embodiment, guiding the user includes providing an instruction to the mobile device to display an indication of a current distance between the mobile device and the object. According to another embodiment, the process includes providing an indication from the mobile device to the user when the specified distance has been reached. According to a further embodiment, providing the indication to the user includes superimposing a first icon indicating the current location of the user on a second icon indicating a second location at the specified distance for conducting the eye examination.

According to another embodiment, the object is a display screen of a second device, and the process includes pairing the mobile device to the second device.

According to another aspect, a process for assessing at least one characteristic of a user's vision is provided. The process includes determining, using the mobile device, a current distance from the mobile device to a display screen; responsive to receiving a first input from the user, determining a testing distance from the mobile device to the display screen; presenting material on the display screen, wherein a size of the material is based at least in part on the testing distance; and receiving a second input from the user in response to the material.

According to one embodiment, the process includes calibrating at least one camera of a mobile device. According to another embodiment, the process includes guiding the user to the testing distance responsive to the first input.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed subject matter. Particular references to examples and embodiments, such as "an embodiment," "an example," "one example," "another embodiment," "another example," "some embodiments," "some examples," "other embodiments," "an alternate embodiment," "various embodiments," "one embodiment," "at least one embodiments," "this and other embodiments" or the like, are not necessarily mutually exclusive and are intended to indicate that a particular feature, structure, or characteristic described in connection with the embodiment or example and may be included in that embodiment or example and other embodiments or examples. The appearances of such terms herein are not necessarily all referring to the same embodiment or example.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

Figure 1:
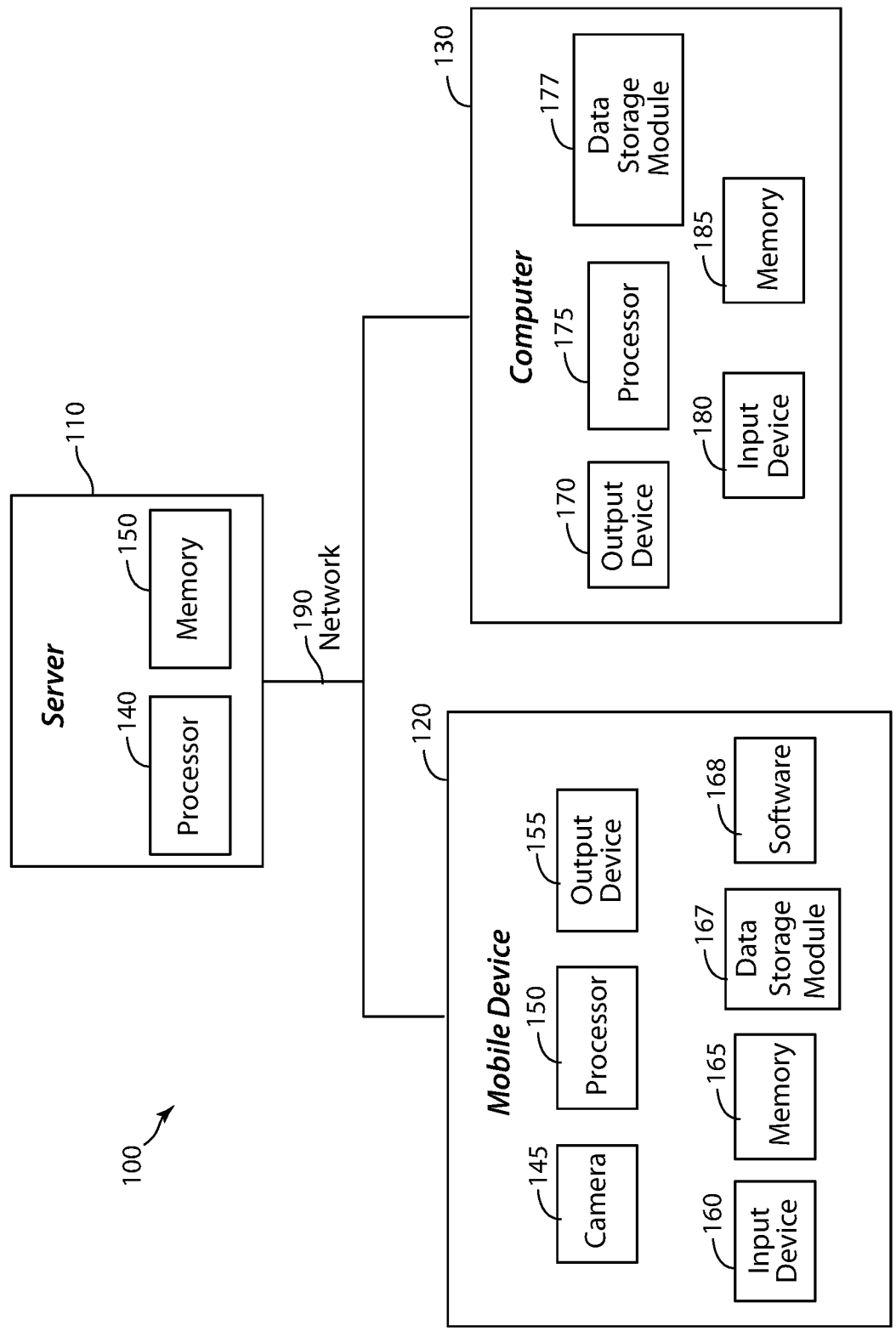
FIG. 1 is a block diagram of an eye examination system according to one or more embodiments.

According to one or more embodiments, the methods and systems disclosed allow a person to easily determine their distance from an object. The target object may be an image of a pattern, an eye exam, or other suitable item. The image may be displayed on a computer screen or other suitable medium such as a printed sheet or series of printed sheets.

According to one or more embodiments, the disclosed methods and systems may guide a person to a specific distance from the object. According to one or more embodiments, the provided guidance may facilitate a user to undergo an eye exam without the need for technical or trained personnel to administer the test. As such, this disclosure opens up the potential for a range of people to receive an accurate eye exam who may have difficulty accessing an optician's office (those that are infirm, remote, etc.), or those who may prefer the convenience of self-administering an exam.

According to one or more embodiments, distance from a target is determined by using a camera capable of running custom software and, according to some examples, displaying feedback to the user (such as may be provided by a smartphone or other mobile or portable device, such as a tablet or laptop computer). According to one or more embodiments, the methods provided do not require specific information about the camera and can be run on most consumer mobile phones or any portable computing device that includes a camera.

According to one or more embodiments, a user may begin the process while positioned close to a displayed pattern, run the application, and point the camera at the calibration pattern. The user then engages in a process for calibrating the camera to determine the camera's intrinsic and extrinsic properties. (Alternatively, the camera's properties may be retrieved programmatically in certain cases.) Calibration of the camera on the mobile device may be carried out according to any methods known to a person of ordinary skill in the art. According to one or more embodiments, calibration requires images of the calibration pattern from multiple angles to determine camera properties. As such, better calibration results can be achieved closer to the pattern where the camera can be moved at a greater angle. In the case that the camera device has other sensors such as an accelerometer, those sensors may be used to make calibration faster or more accurate.

The calibration pattern may be an object with a known geometry and easily detectable feature points. According to some embodiments a chessboard pattern is used. The calibration process may determine certain intrinsic properties of the camera such as those relating to focal length, image sensor format, and principal point. The calibration aids in relating pixel count of an object to actual dimensions. The results of the calibration may be used to determine the distance between the camera and a target. By using an easily identifiable pattern or shape one may accurately then track the distance from the target to the camera as one is moved in relation to the other.

According to one or more embodiments, the pattern is presented on an electronic display. However, it is to be understood that any medium for the pattern, including paper, can be used. Furthermore, the calibration pattern and the eye exam chart may be displayed on the same monitor or on separate displays, and may be collectively referred to as an object or target object. Unless stated otherwise, the terms "eye exam material" and "eye exam chart" may be understood to encompass any image, static or dynamic, associated with determining one or more characteristics of a test subject's vision.

In the case where the calibration pattern is on a piece of paper, the chessboard itself or an eye chart can be used as a target during the tracking stage, during which the camera is moving. In the case where the chessboard pattern is on a computer screen, after calibration the screen can be changed to solid white so that the target is large and is not blurred by lighting contrast or glare as the camera of the mobile device is moved.

In the case where the calibration pattern is displayed on a computer screen, the mobile device can be linked to a web page or application running on the computer such that the mobile device can be used to control the application on the computer. This can be helpful for guiding the user through the calibration process and also for guiding the user through an eye exam.

In the case where the calibration pattern and exam chart are each on a piece of paper, all instruction can be given through the mobile device.

Once the properties of the mobile device's camera are determined, either through calibration or through a retrieval process, the physical distance to the screen may be determined. Calibration of the camera gives a full transformation from three-dimensional space to a two-dimensional projection, where one can solve for the distance in three-dimensional space given the size of an object in three-dimensional space and its size in the two-dimensional projection. The application of this transformation can be simplified by using only the focal constant from the intrinsic matrix. The size in pixels of the monitor is inversely proportional to the physical distance from the camera, with a proportionality constant given by the intrinsic matrix, determined through calibration or some other means, and the known physical size of the object. Such a calculation allows for the distance to be tracked, as the mobile device is moved.

Turning to the figures, FIG. 1 illustrates a block diagram of an eye examination system 100 according to one or more embodiments. In the embodiment shown in FIG. 1, the system 100 comprises a server 110 in communication with a first device 120 and a second device 130. As shown, the first device 120 is coupled to, and can exchange data with, server 110 and computing device 130 via network 190. In addition, according to this example, the first device 120 includes a camera 145, a processor 150 coupled to the camera, an output device 155, such as a monitor or display screen or audio speaker, an input device 160, such as a touch surface, a keyboard, microphone, or a mouse, a data storage module 167, and a memory 165 coupled to the processor 150. The first device 120 also includes camera calibration and eye examination software 168.

The server 110 includes one or more computing devices located remote or local to the first and second devices 120 and 130. The server includes a processor 140 and a memory 142 coupled to the processor. In one example, the memory 142 includes volatile memory, such as RAM, and non-volatile memory, such as a magnetic disk.

The second device 130 is coupled to, and can exchange data with, server 110 and mobile device 120 via network 190. In addition, according to this example, the second device 130 includes processor 175, a data storage module 177, a memory 185 coupled to the processor 175, an output device 170, such as a monitor or display screen or audio speaker, and an input device 180, such as a touch surface, a keyboard, microphone, or a mouse.

The first device 120 is a portable computing device. For example, it may be a mobile device, such as a smart phone, tablet, or laptop computer, all of which are encompassed by the terms "portable computing device" or "mobile device." The mobile device 120 is capable of delivering and/or receiving data to or from server 110. The second device 130 may be a portable computing device, like any of those described for the first device 120, or a stationary computing device. Unless specified otherwise, the terms "monitor" or "display screen" may be understood to encompass any visual display associated with a portable or stationary computing device.

The server 110 exchanges data with the first and second devices 120 and 130. This data may be exchanged through an installed program in the first or second device 120 or 130, or through a web page loaded on the first or second device 120 or 130.

In use, the first and second devices 120 and 130 may be used in conjunction to determine the distance between the two devices. The output display 170 of the second device 130 may be used to display a calibration pattern, a substantially blank screen for distance tracking, and/or an eye examination chart. The images displayed on the monitor 170 may be provided to the monitor 170 by the server 110 in response to instructions received from the server 110, and the particular instructions provided to the monitor 170 may be based on information received from the camera device 120. A pairing of the first and second devices 120 and 130, as further discussed below, may facilitate their coordination.

The computing device 130, as shown in FIG. 1 is internet-enabled and the various patterns, images, or testing material displayed is provided through a web-page, in response to output from the first device 120. In alternative embodiments, an application or program running on the computer 130 is responsible for the content displayed.

Figure 10:
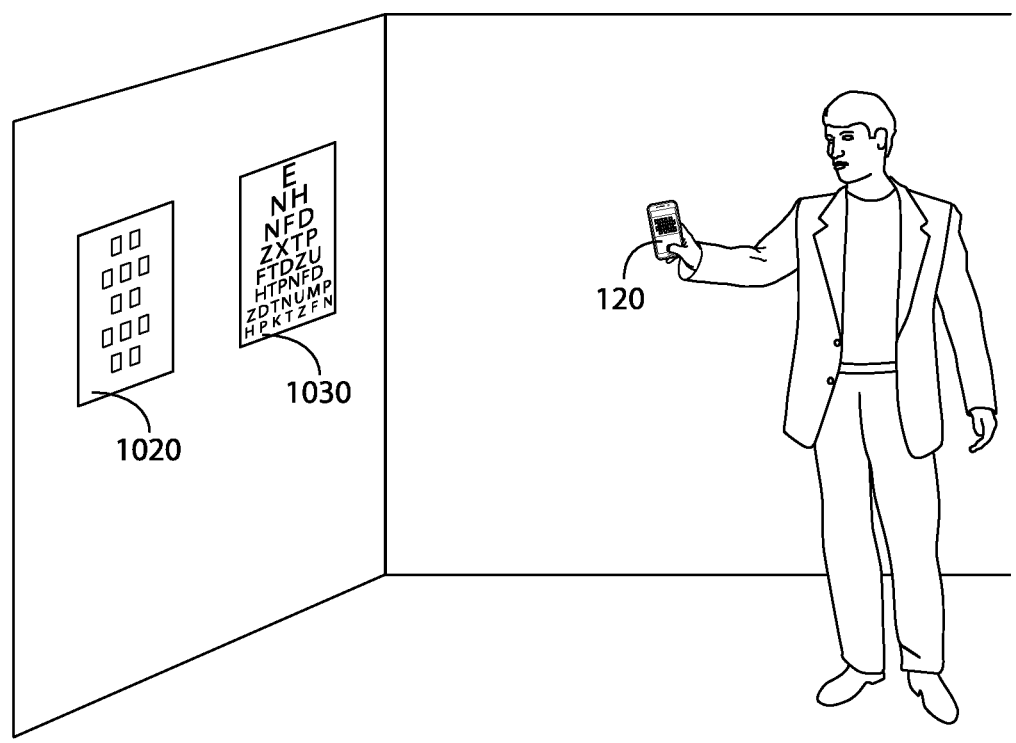
FIG. 10 is an illustration of an embodiment in which a calibration chart and an eye exam chart are displayed on printed paper.

While in the system 100 shown in FIG. 1 both the first device 120 and the second device 130 are in communication with the server 110, alternative configurations are also considered within the scope of the present disclosure. For example, according to certain embodiments the device 120 including the camera 145 and/or the second device 130 may not be in communication with a server 110 or each other. For example, all the instructions required by the camera device 120 may already be stored on device 120. Likewise, information or instructions for what to display on the second device 130 may be provided without requiring communication over a network. Also, the second device 130 may be in direct communication with the first device 120 using one of a number of known wireless protocols. Furthermore, as discussed elsewhere, according to certain embodiments the second device 130 may comprise simply an image printed on a sheet of paper. FIG. 10, for example, shows an alternative, simplified embodiment where the second device comprises a target calibration pattern 1020 and eye chart 1030 printed out and attached to a wall. A software-enabled camera device 120 is still used to track distance and guide a user to a specified position.

According to one or more embodiments, a system like that shown in FIG. 1 is implemented in processes directed to self-administered eye examination.

Figure 2:
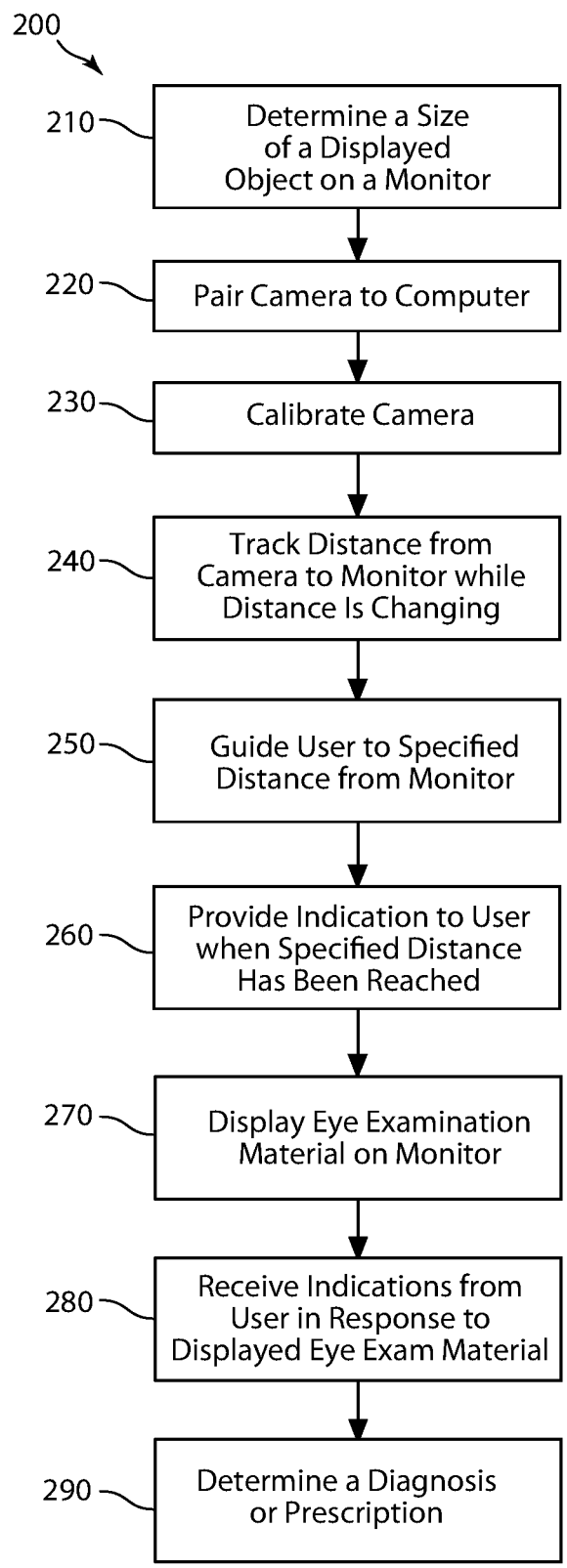
FIG. 2 is a flow chart of a method for determining a diagnosis or lens prescription according to one or more embodiments.

FIG. 2 is a flow chart of a process 200 for determining a diagnosis or lens prescription according to one or more embodiments. One or more embodiments of the process 200 may be implemented using a system like that shown in FIG. 1.

A first step 210 of the process 200 includes determining an object display size on an output device, such as output device 170 of computing device 130. Where the screen is a computer monitor, the step may include displaying an object on the screen and receiving input from a user resizing the object until its dimensions match a reference object of known dimensions. The reference object may be any object readily available and having a standardized shape. For example, the reference object may be a ruler or a credit card. The object may also include other configurations such as a line. In other embodiments, step 210 may be omitted, if the characteristics of the monitor are known, or an electronic screen is not being used.

Figure 4:
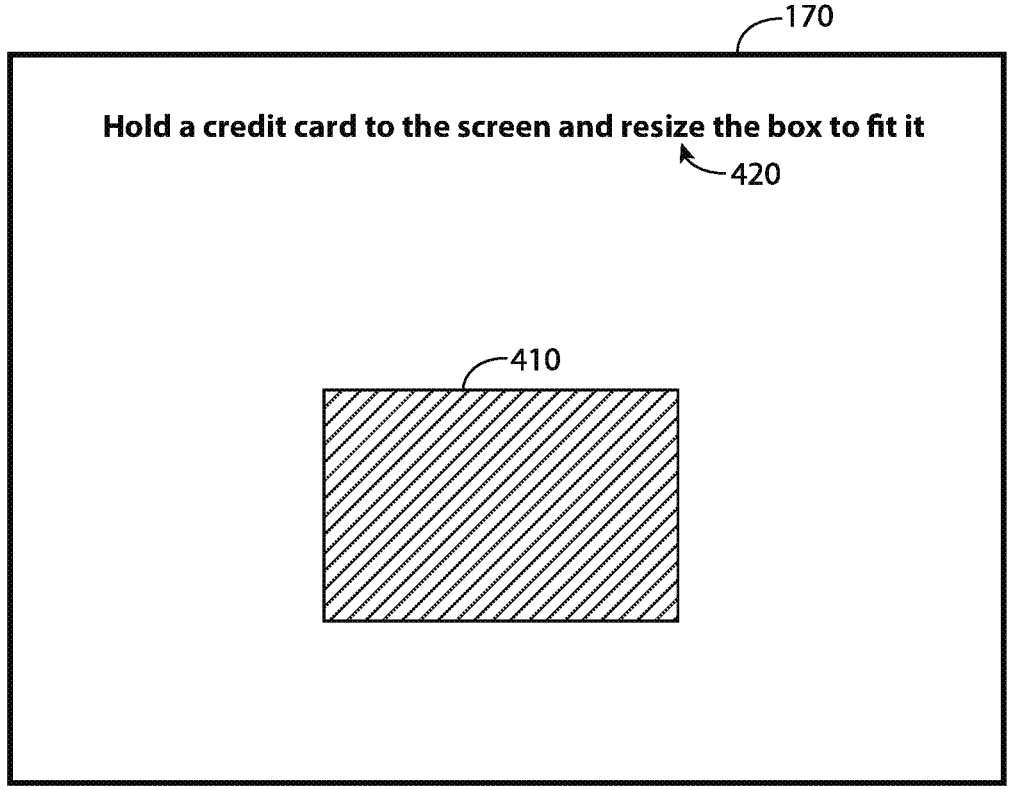
FIG. 4 is an illustration of a user interface during a screen size determination step according to one or more embodiments.

FIG. 4 is an illustration of a user interface during the step of determining an object display size according to one or more embodiments. According to the embodiment shown, a screen 170 of the target device, computer 130 includes both a sizing shape 410 and instructions 420 for using the shape 410 with a reference object, in this example, a standard credit card, to determine screen size. In this example, a user holds a credit card to the screen and using a mouse or other user interface device resizes the box 410 to be the same as the outer perimeter of the credit card.

Step 220 of the process 200 includes pairing the camera of the portable device 120, with the computer 130. The step of pairing facilitates the coordination of instructions and information between the portable device 120 and the computer 130, but in some embodiments, this step is not used. Once paired, the server 110 may deliver instructions to the computer 130 directing what images are displayed on its monitor 170 in response to information received from the camera 145 of the device 120. The step of pairing may be achieved by any technique known to one of ordinary skill in the art that will allow the server 110 to associate the portable device 120 with the computer 130. For example, an identifier may be displayed on the monitor 170 of computer 130 and captured by the camera of device 120 or vice versa. In some embodiments a QR code is displayed on the monitor 170. The camera then captures an image of the code and transmits it to the server 110, allowing the server 110 to match the two devices 120 and 130 and coordinate the instructions sent to each.

Figure 5A:
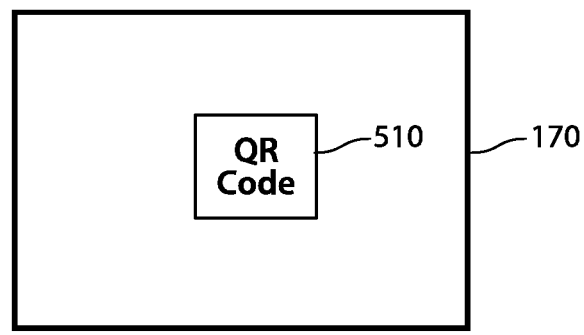
FIGS. 5A and 5B are illustrations of a user interface during a device pairing step according to one or more embodiments.
Figure 5B:
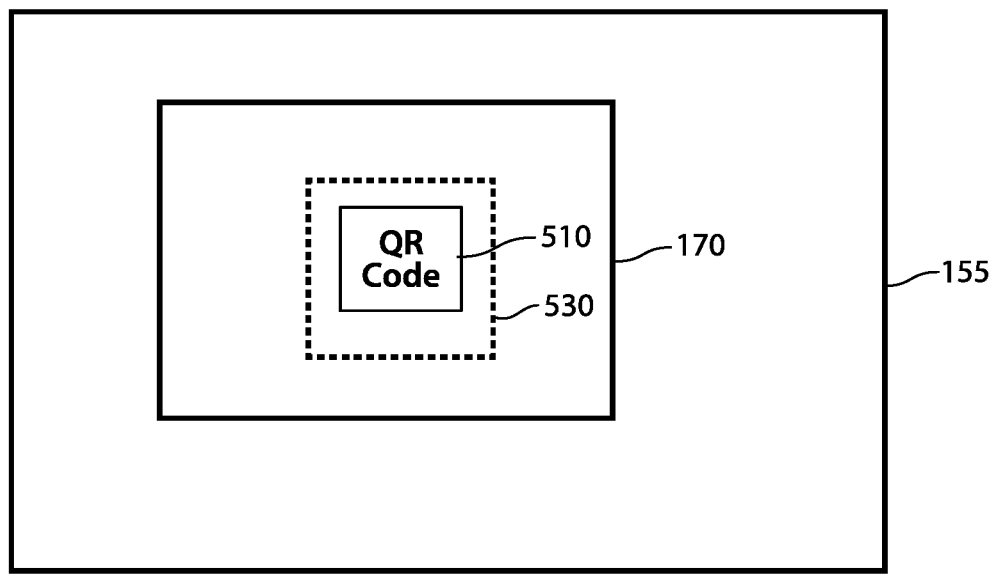

FIGS. 5A and 5B illustrate user interfaces during a device pairing step according to one or more embodiments. In FIG. 5A a monitor 170 of computer 130 displays a QR code 510. In FIG. 5B the viewfinder of camera 145, which may be displayed on the output device 155, displays the monitor 170 with the QR code 510 within. The code 510 is positioned within the viewfinder's target box 530. The code is identified and the two devices 120 and 130 are paired so that output and input between the two devices 120 and 130 may be coordinated. In one embodiment, the QR code may be generated by the server 110 and provided to the device 130, while in other embodiments, the device 130 may generate the QR code and provide it to the server 110. In other embodiments, images other than QR codes may be used to pair the devices, and other identifiers may also be used. For example, a string of letters and or numbers can be displayed on one of devices 120 and 130, and entered in the other of the devices 120 and 130 to pair the devices.

Step 230 of the process 200 includes calibrating the camera to determine certain characteristics of the camera 145, and using that information to standardize measurements made using the camera 145. Any process for calibrating a camera 145 known to a person of ordinary skill in the art may be utilized. In other embodiments, the characteristics of the camera 145 may be known, for example, based on the model of the mobile device 120 used, and calibration of the camera 145 may not be necessary, where, for example, the properties of the camera model may be retrieved from a program.

Figure 6:
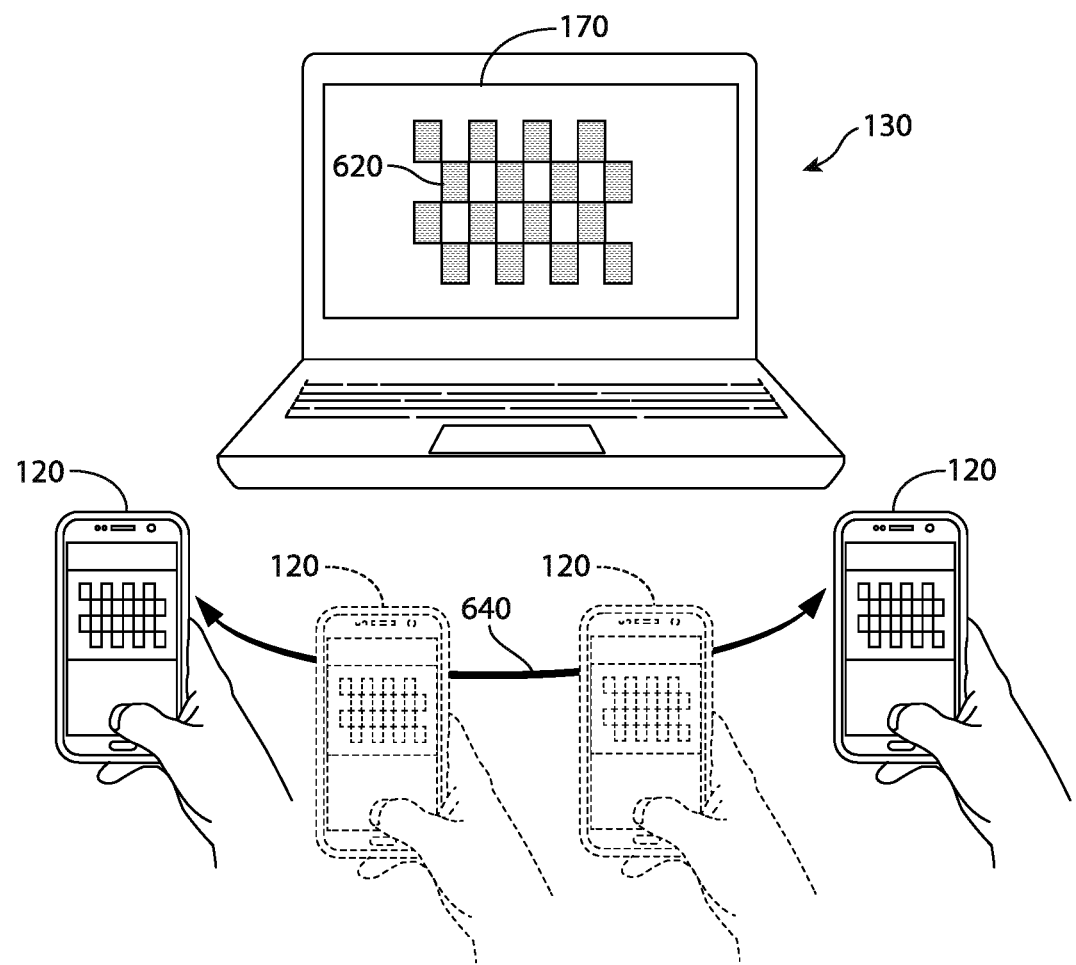
FIG. 6 is illustration of a camera calibration step according to one or more embodiments.

FIG. 6 is an illustration of a camera calibration step according to one or more embodiments. A calibration pattern 620 is displayed on the monitor 170 of computer 130. In the embodiment shown in FIG. 6, a chessboard pattern is displayed, but other patterns may be displayed according to other embodiments. The camera 145 of the device 120 may then be used to capture images of the pattern 620 at various angles, for example, by sweeping the camera around the pattern in a sweeping motion, for example along an arc 640. The information gathered from the images is then processed to determine characteristics of the camera 145. Once the camera 145 is calibrated its distance from the monitor 610 may be calculated.

Step 240 of the process 200 includes tracking the distance from the device 120 to the monitor 170 of computer 130 as the device 120 is moved away from or toward the monitor 170 with the camera 145 of device 120 trained on the monitor 170. As a user holding the camera 145 moves in relation to the monitor 170, the monitor 170 may be maintained in the camera viewfinder. As the distance changes, the portion of the viewfinder taken up by the monitor 170 will also change. This data may be used along with the initial distance determination to track the current distance of the camera 145 from the monitor 170 on a near real time basis.

Step 250 of the process 200 includes guiding a user holding the mobile device 120 to a specific distance from the monitor 170. Guiding may comprise providing an indication to the user equipped with the mobile device 120 of the current distance from the monitor 170 (determined as a result of the tracking step 240). Guiding may further comprise providing an indication as to where the user is in a relation to a specified end-point distance that the user is attempting to reach, to aid the user in determining whether to continue to move away from the monitor 170. Guiding may further comprise providing instructions to the user to continue to move to or from the monitor 170. These instructions may be provided on the monitor 170 of the computer 130 or on an output display 155 of the mobile device 120, or conveyed audibly.

Figure 7A:
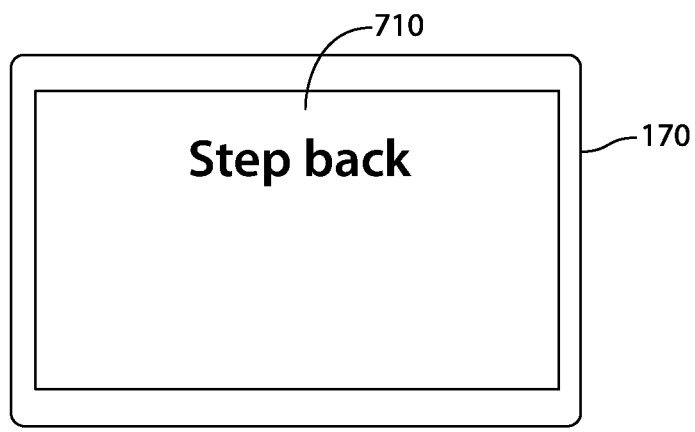
FIGS. 7A and 7B are illustrations of a user interface during a guiding step according to one or more embodiments.
Figure 7B:
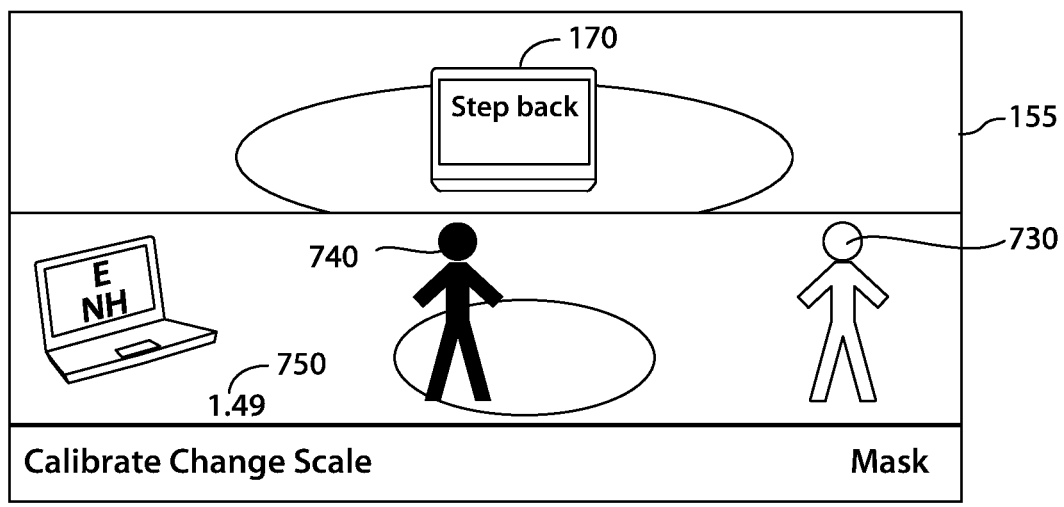

FIGS. 7A and 7B are illustrations of a user interface during a guiding step according to one or more embodiments. In FIG. 7A monitor 170, which is paired with the mobile device 120, provides instructions 710 guiding a user to "Step back" since the desired distance has not yet been reached. FIG. 7B illustrates a display 155 on the camera device 120. In addition to maintaining the monitor 170 in the camera viewfinder, the display 150 also displays a current distance 750 from the monitor 700 and an icon 730 representative of a person standing at a desired distance and an icon 740 representative of the user to aid in guiding the user to the desired distance. In at least one embodiment, the icon 740 moves towards the icon 730 as the user moves towards the desired distance.

Figure 8A:
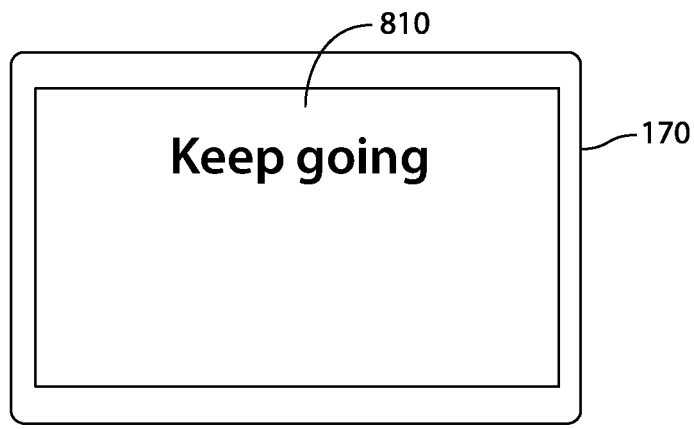
FIGS. 8A and 8B are illustrations of a user interface during a guiding step according to one or more embodiments.
Figure 8B:
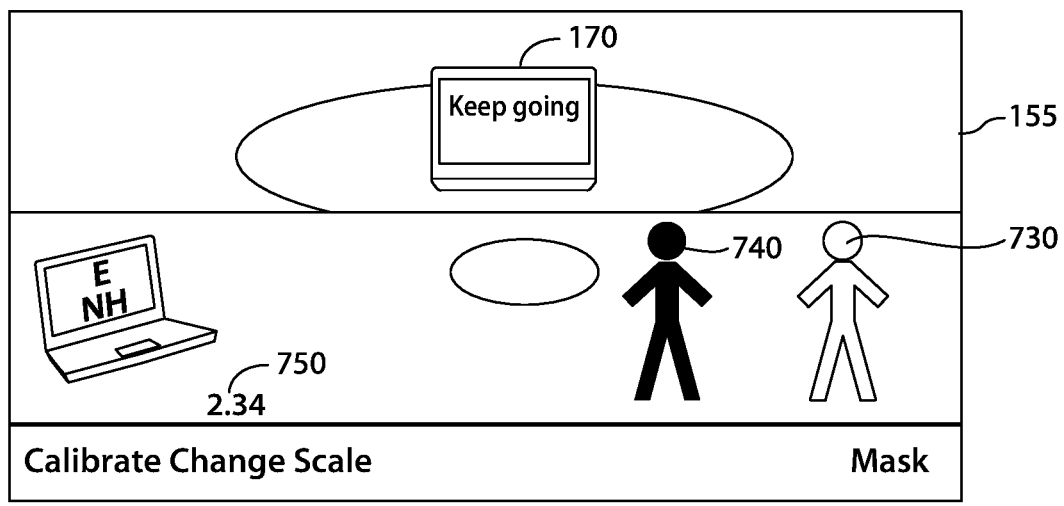

FIGS. 8A and 8B are other illustrations of a user interface during a guiding step according to one or more embodiments, as the user continues to move toward the desired position shown in FIG. 7B. In FIG. 8A monitor 170, which is paired with the camera device 120, provides new instructions 810 guiding a user to "Keep going" since the desired distance has not yet been reached. FIG. 8B illustrates a display 155 on the camera device 120. In addition to maintaining the monitor 170 in the camera viewfinder, the display 155 also displays a current distance 750 from the monitor 170 and an icon 730 representative of a person standing at a desired distance and an icon 740 representative of the user to aid in guiding the user to the desired distance.

The specific distance from the monitor that the user is attempting to reach may be a fixed distance determined as required by the particular application. In the context of providing an eye examination, a particular eye test may require that the user be at a specific distance, for example ten feet from the monitor displaying an eye chart, give or take some acceptable range of error, which may be one foot or ten percent of the total distance according to certain embodiments. Alternatively, the specific distance may be a function of the displayed object size determined in step 210. Where the displayed object is found to be smaller, the specified end-distance from the monitor may be shorter, as the items displayed on the monitor will be smaller. Alternatively, the results of step 210 may be used to display letters of a fixed size, allowing the same distance to be used regardless of the screen size.

As the mobile device 120 is moved in relation to the screen 170, ultimately, the designated distance from the screen 170 is reached. Step 260 of the process 200 includes providing an indication to a user once the designated distance has been reached. The indication may be a display on the monitor 170 or an output device 155 of the mobile device 120 of any general type that would allow a user to know that he or she can stop moving in relation to the monitor.

Figure 9A:
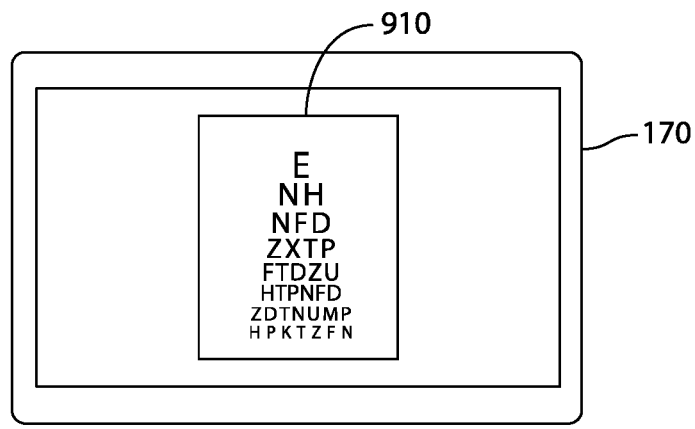
FIGS. 9A and 9B are illustrations of a user interface during a step of indicating that a designated distance has been reached according to one or more embodiments.
Figure 9B:
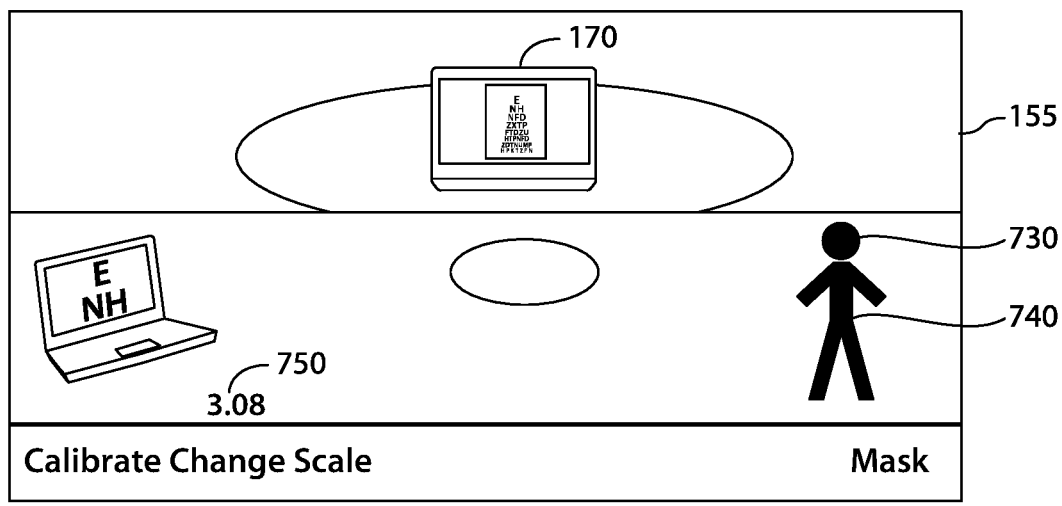

FIGS. 9A and 9B are illustrations of a user interface during a step of indicating that a designated distance has been reached, according to one or more embodiments. In FIG. 9A monitor 170, which is paired with the camera device 120, displays an eye chart 910 to indicate the specified distance has been reached. FIG. 9B illustrates a display 155 on the camera device 120. In addition to maintaining the monitor 170 in the camera viewfinder, the display 155 also displays a current distance 750 from the monitor 170 and shows superimposed icons 730 and 740 of a person standing at the desired distance and of the user, respectively, thereby providing indication that the specified distance has been reached.

In the context of an eye examination, the distance from the eye to the eye test chart may be slightly different from the distance between the camera and the testing display depending on the positioning of the camera by the user relative to the user's eyes. In some embodiments, the user may be instructed to position the camera near the user's eyes to reduce this error, or the system may include an adjustment to the measurement distance based on a typical distance between the position at which the user holds the camera and the user's eyes. Nevertheless, this difference is generally within an acceptable range of error and therefore does not harm the integrity of the test. Unless stated otherwise, the phrase "specified distance" and related terms are understood to include a distance within a reasonable range of error. According to some embodiments, the range of error may be one foot or ten percent of the total distance, whichever is greater.

At step 270 of process 200, eye examination material is displayed on the monitor 170 and the eye test or a new phase of the eye test may begin. In embodiments which include a step of pairing the camera device 120 to the computer 130, the eye exam material may automatically be displayed once the designated distance is reached.

A variety of different eye tests may be implemented in step 270, depending on the needs of the user. Tests may include: tests of visual acuity; both cylindrical power and spherical power tests; tests for peripheral vision or color blindness; tests for astigmatism, cataracts and various pathologies or diseases, etc. Tests may be static or dynamic. Specific examples of testing material include, without limitation: Snellen charts; E charts; Landoldt C charts, etc.

During testing, at step 280 of process 200 indications are received from the user in response to the displayed eye exam material. The indications may be in the form of vocal or typed responses or any suitable input. The indications may be in response to a prompt provided to the user by one or both of devices 120 and 130. The prompt may include text on one of the screens and/or an audio prompt. The prompt may display or state a command such as "read the second line of characters on the eye chart."

The process 200 may include a step of determining a diagnosis or prescription 290 based on the test subject's responses. The determination may be conducted automatically by one of the devices 120 and 130 or by the server. The determination may also be done by an optometrist that receives results of the test from the server 110, for example, over the Internet.

Figure 3:
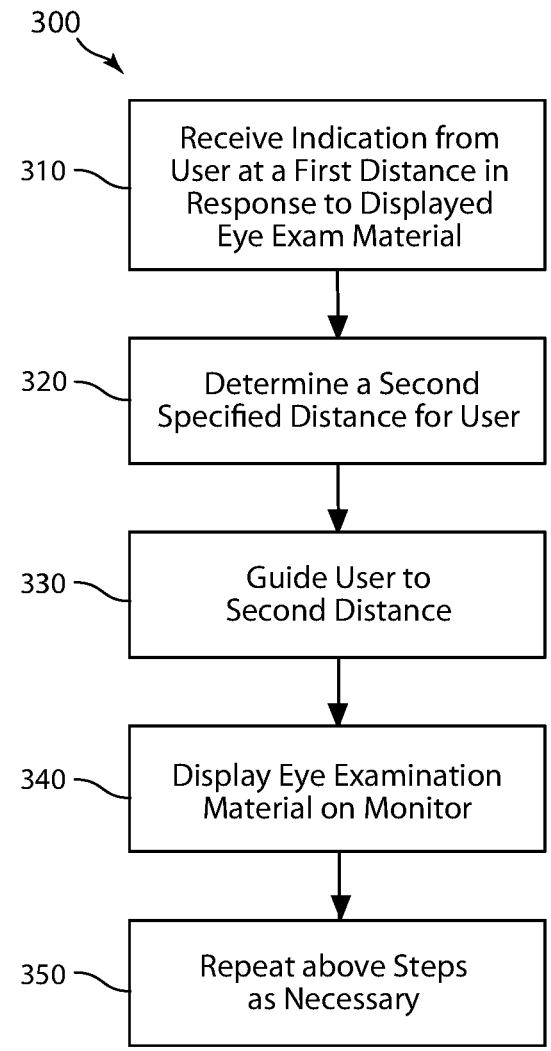
FIG. 3 is a flow chart of a method for repositioning a test subject according to one or more embodiments.

In one alternative embodiment, a process 300, shown in FIG. 3, is provided for directing a test subject to two or more distances from the eye exam chart over the course of the examination. As shown in the flow chart in FIG. 3, the process includes a step 310 of receiving indications from the test subject at a first distance in response to displayed eye examination material. The process 300 may occur after the process 200. In particular, the process 300 may be used based on a user's results or partial results to an eye examination performed using process 200. In particular, if the user is at too great a distance to be able to properly read a displayed chart, based on the user's eye sight, the process 300 may be used to conduct an eye exam at a closer distance from the displayed eye chart.

A second specified distance for the test subject is determined using a step 320 of process 300. This second distance may be determined in consideration of various factors. According to some embodiments, this determination may be made after ascertaining that the first distance is inappropriate. For example, if the user/test subject's eyesight is especially poor, then the user may not be able to engage in a meaningful eye examination from the first distance, and steps may be taken to have the user move closer. Alternatively, if the examination is too easy and therefore not allowing for the provision of appropriate feedback, it may be required that a user move to a second distance that is greater than the first distance. In some embodiments, the step of determining and guiding a test subject to one or more additional distances may be in response to the requirements of a battery of tests. According to some embodiments, the determination of the second distance may be advantageous, where one eye test in a battery of tests provides more reliable results if performed at a second distance different from the first distance at which one or more tests were carried out.

Once a second distance is determined, the test subject may be guided to the second distance according to a step 330. The step 330 may be carried out in a manner corresponding to steps 240, 250, and 260 of the process 200, as shown in the flow chart of FIG. 2.

Once the test subject has reached the new position, a step 340 of displaying the eye examination material may take place. As discussed above, this material may be the same material as displayed when the test subject was at the first position or it may be new material. In at least one embodiment, the user is prompted to move to the additional test locations using the process described with reference to FIGS. 7 and 8.

Finally, the steps of repositioning may be repeated as necessary to place the test subject in a third position, fourth position, etc., as provided for in step 350.

According to another alternative embodiment, a final distance from the user to the test material is not predetermined. Instead, according to process 1100, as shown in the flow chart in FIG. 11, the user moves to a distance of his choice from the monitor and undertakes an eye examination from that distance. The basis of the user's choice of the testing distance may be a variety of factors, such as limited room space. Or the user may choose the testing distance based on when an image displayed on the monitor becomes recognizable. Alternatively, the choice of distance may be arbitrary.

Figure 11:
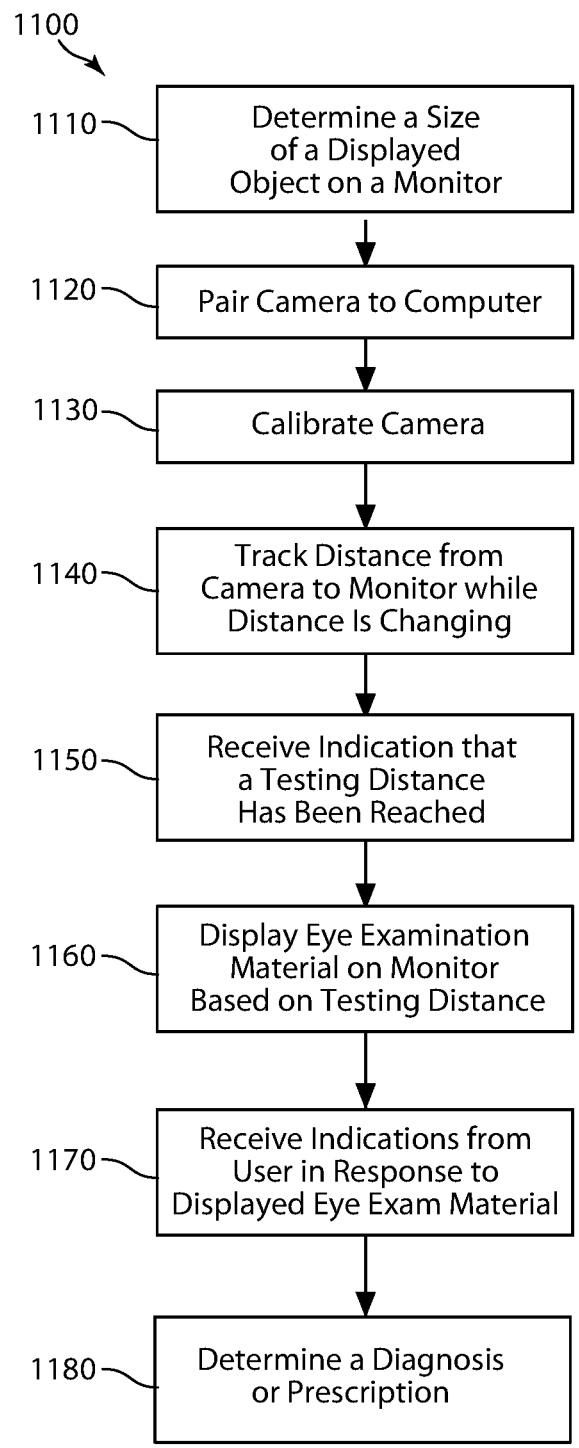
FIG. 11 is a flow chart of an alternative method for conducting an eye examination according to one or more embodiments.

As shown in the flow chart in FIG. 11, the initial steps 1110, 1120, 1130, and 1140 are similar to the initial steps shown in FIG. 2. However, instead of guiding a user to a specified distance from the monitor, the method incorporates a step 1150 of receiving indication that a testing distance has been reached. Indication may be in the form of direct user input into the camera-enabled mobile device. Alternatively, indication may be in the form of the mobile device detecting no change in distance for a period of time, for example, three seconds or more.

Once the system has received indication that the testing distance has been reached, the step 1160 of displaying eye exam material on the monitor is carried out. Characteristics of the displayed material, such as their display size, are based on the determined testing distance. For example, the closer the user is to the monitor, the smaller the size of the displayed testing materials. Conversely, the further the user is from the monitor, the larger the display size.

Figure 12:
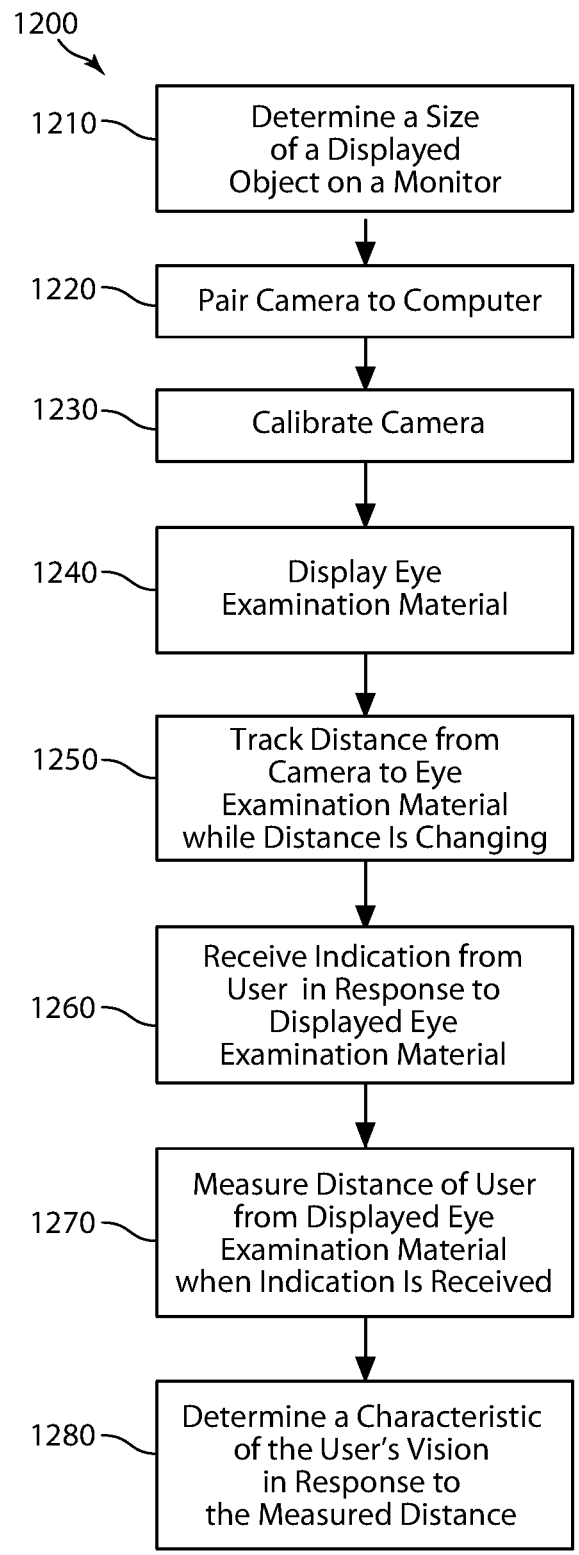
FIG. 12 is a flow chart of an alternative method for conducting an eye examination according to one or more embodiments.

According to another alternative embodiment, the user may change his distance from the screen in response to the material presented on the screen as part of a testing procedure. For example an image may be presented on the screen, and the user may be directed to walk to a distance where he can see this object clearly. That distance is noted by the system and aids in determining a characteristic of the user's vision. FIG. 12 shows a flow diagram of a process 1200 incorporating this embodiment. The initial steps 1210, 1220, and 1230 are similar to corresponding steps discuss in relation to FIG. 2. In step 1240 eye examination material is displayed. The user then moves to or from the displayed material, with the mobile device in hand, while, according to step 1250, the distance to the eye examination material is tracked. The user then stops when reaching a certain distance, such as when he can see the displayed object clearly. According to step 1260 of the process, the system then received indication from the user in response to the displayed eye examination material. The indication may be in the form of direct user input into the mobile device. Alternatively, indication may be in the form of the mobile device detecting no change in distance for a period of time, for example, three seconds or more. At this point, in step 1270, the user's distance from the eye exam material is measured. This measured distance is then used, at least in part, to determine a characteristic of the user's vision, in step 1280.

Figure 13:
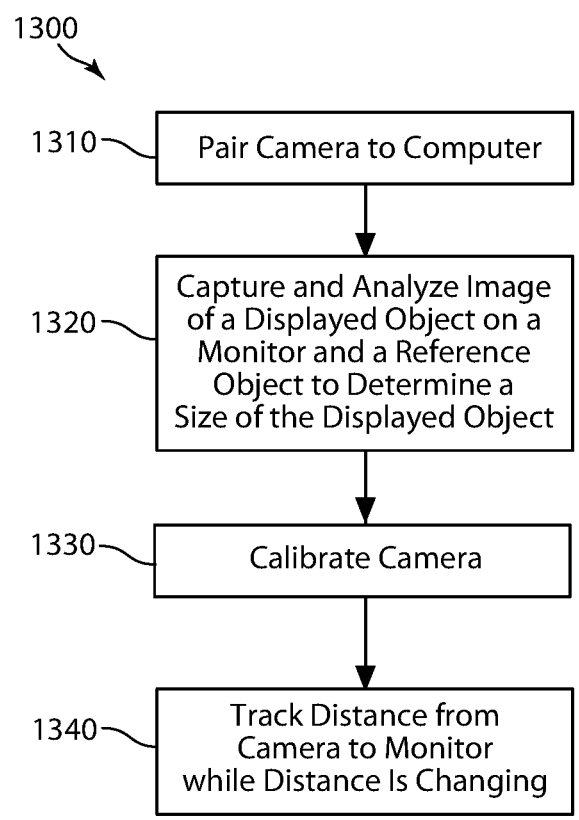
FIG. 13 is a flow chart of an alternative method for determining a size of a displayed object on a monitor.

According to an alternative process, the size of a display object on the monitor may be determined with minimal input from the user, as shown in FIG. 13. According to the alternative process, the step of pairing devices 1310, similar to that described above in reference to step 220 of FIG. 2, precedes the step 1320 of determining a displayed object size. Like the embodiment described in conjunction with FIG. 4, a shape, for example, a rectangle, is displayed on the monitor screen, and the user positions a reference object of a known size, such as a credit card, against the sizing shape. The user, using the camera of the mobile device, then captures one or more images of the credit card against the rectangle. The images are then analyzed to determine the size of the displayed object on the computer screen relative to the size of the reference object positioned against the screen. Based on this information and the link between the mobile device and the computer associated with the monitor, the size of the display object may be determined without any further input from the user. The process 1300 may continue with a calibration step 1330 (which can also precede steps 1310 and 1320) and move on to a distance tracking step 1340. The alternative process 1300 of determining screen object size may be incorporated into any of the described eye examination processes or any alternative application of the disclosed methods, as would be understood by a person of ordinary skill in the art.

As discussed above, aspects and functions disclosed herein may be implemented as hardware or software on one or more of these computer systems. There are many examples of computer systems that are currently in use. These examples include, among others, network appliances, personal computers, workstations, mainframes, networked clients, servers, media servers, application servers, database servers and web servers. Other examples of computer systems may include mobile computing devices, such as cellular phones and personal digital assistants, and network equipment, such as load balancers, routers and switches. Further, aspects may be located on a single computer system or may be distributed among a plurality of computer systems connected to one or more communications networks.

For example, various aspects and functions may be distributed among one or more computer systems configured to provide a service to one or more client computers. Additionally, aspects may be performed on a client-server or multi-tier system that includes components distributed among one or more server systems that perform various functions. Consequently, examples are not limited to executing on any particular system or group of systems. Further, aspects may be implemented in software, hardware or firmware, or any combination thereof. Thus, aspects may be implemented within methods, acts, systems, system elements and components using a variety of hardware and software configurations, and examples are not limited to any particular distributed architecture, network, or communication protocol.

As shown, the computer devices 110, 120, and 130 are interconnected by, and may exchange data through, communication a network 190. The network 190 may include any communication network through which computer systems may exchange data. To exchange data using the network 190, the computer systems 110, 120, and 130 and the network 190 may use various methods, protocols and standards, including, among others, Fibre Channel, Token Ring, Ethernet, Wireless Ethernet, Bluetooth, IP, IPV6, TCP/IP, UDP, DTN, HTTP, FTP, SNMP, SMS, MMS, SS7, JSON, SOAP, CORBA, REST and Web Services. To ensure data transfer is secure, the computer systems 110, 120, and 130 may transmit data via the network 190 using a variety of security measures including, for example, TSL, SSL or VPN.

As discussed above with regard to FIG. 1, various aspects and functions may be implemented as specialized hardware or software executing in one or more computer systems. As illustrated in FIG. 1, the device 120 includes a processor 150, a memory 165, a camera 145, an output display 155, a data storage module 167, and an input device 160. (The following detailed description of the components of mobile device 120, may be generally understood to also apply to corresponding structure present in computer 130 or server 110.)

The processor 150 may perform a series of instructions that result in manipulated data. The processor 150 may be a commercially available processor such as an Intel Xeon, Itanium, Core, Celeron, Pentium, AMD Opteron, Sun Ultra-SPARC, IBM Power5+, or IBM mainframe chip, but may be any type of processor, multiprocessor or controller. The processor 150 is connected to other system elements, including one or more memory devices 165, the camera 145, etc.

The memory 165 may be used for storing programs and data during operation of the device 120. Thus, the memory 165 may be a relatively high performance, volatile, random access memory such as a dynamic random access memory (DRAM) or static memory (SRAM). However, the memory 165 may include any device for storing data, such as a disk drive or other non-volatile storage device. Various examples may organize the memory 165 into particularized and, in some cases, unique structures to perform the functions disclosed herein.

The mobile device 120 also includes one or more interface devices such as input devices 160 and output devices 155. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system 120 to exchange information and communicate with external entities, such as users and other systems.

The data storage 167 may include a computer readable and writeable nonvolatile (non-transitory) data storage medium in which instructions are stored that define a program that may be executed by the processor 150. The data storage 167 also may include information that is recorded, on or in, the medium, and this information may be processed by the processor 150 during execution of the program. More specifically, the information may be stored in one or more data structures specifically configured to conserve storage space or increase data exchange performance. The instructions may be persistently stored as encoded signals, and the instructions may cause the processor 150 to perform any of the functions described herein. The medium may, for example, be optical disk, magnetic disk or flash memory, among others. In operation, the processor 150 or some other controller may cause data to be read from the nonvolatile recording medium into another memory, such as the memory 165, that allows for faster access to the information by the processor 150 than does the storage medium included in the data storage 167. The memory may be located in the data storage 167 or in the memory 165, however, the processor 150 may manipulate the data within the memory 165, and then copy the data to the storage medium associated with the data storage 167 after processing is completed. A variety of components may manage data movement between the storage medium and other memory elements and examples are not limited to particular data management components. Further, examples are not limited to a particular memory system or data storage system.

Although the device 120 is shown by way of example as one type of a computer device upon which various aspects and functions may be practiced, aspects are not limited to being implemented on the device 120 as shown in FIG. 1. Various aspects and functions may be practiced on one or more computers having a different architectures or components than that shown in FIG. 1. For instance, the device 120 may include specially programmed, special-purpose hardware, such as for example, an application-specific integrated circuit (ASIC) tailored to perform a particular operation disclosed herein. While another example may perform the same function using a grid of several general-purpose computing devices running MAC OS System X with Motorola PowerPC processors and several specialized computing devices running proprietary hardware and operating systems.

The device 120 may include an operating system that manages at least a portion of the hardware elements included in the device 120. Usually, a processor or controller, such as the processor 150, executes an operating system which may be, for example, a Windows-based operating system, such as, Windows NT, Windows 2000 (Windows ME), Windows XP, Windows Vista or Windows 7operating systems, available from the Microsoft Corporation, a MAC OS System X operating system available from Apple Computer, one of many Linux-based operating system distributions, for example, the Enterprise Linux operating system available from Red Hat Inc., a Solaris operating system available from Sun Microsystems, or a UNIX operating systems available from various sources. Many other operating systems may be used, and examples are not limited to any particular implementation.

The processor 150 and operating system together define a computer platform for which application programs in high-level programming languages may be written. These component applications may be executable, intermediate, byte-code or interpreted code which communicates over a communication network, for example, the Internet, using a communication protocol, for example, TCP/IP. Similarly, aspects may be implemented using an object-oriented programming language, such as .Net, SmallTalk, Java, C++, Ada, or C # (C-Sharp). Other object-oriented programming languages may also be used. Alternatively, functional, scripting, or logical programming languages may be used.

Additionally, various aspects and functions may be implemented in a non-programmed environment, for example, documents created in HTML, XML or other format that, when viewed in a window of a browser program, render aspects of a graphical-user interface or perform other functions. Further, various examples may be implemented as programmed or non-programmed elements, or any combination thereof. For example, a web page may be implemented using HTML while a data object called from within the web page may be written in C++. Thus, the examples are not limited to a specific programming language and any suitable programming language could be used. Thus, functional components disclosed herein may include a wide variety of elements, e.g. executable code, data structures or objects, configured to perform described functions.

Embodiments described above utilize a process for determining distance between two objects in conjunction with the performance of an eye exam. Other embodiments may be used to determine distance for a number of different applications including: providing directions or orientation guidance for use in a retail store or other location to allow a user to find a specific location or object relative to the screen; games in which a player must throw something at a target a certain distance away from their present location; visualizing the size of an object that might be later placed in that space (such as furniture in a room); or other applications which require a user to determine absolute distances or sizes. Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. An eye examination system, comprising:
    a server, the server configured to:
        provide, to a first computer over a network, instructions to display a resizable box on a monitor of the first computer;
        provide, to the first computer over the network, instructions to display user instructions to place a reference object against the monitor in the resizable box and adjust a size of the resizable box to match a size of the reference object;
        determine, based on the size of the resizable box that matches the size of the reference object, a size of the monitor;
        provide, to the first computer over the network, instructions to display a camera calibration pattern on the monitor, the instructions based on the determined size of the monitor;
        provide, to a second computer over the network, instructions to display user instructions to capture an image of the camera calibration pattern;
        receive, from the second computer, an indication that the second computer is at a desired location;
        provide, to the first computer over the network and responsive to receiving the indication from the second computer, instructions to display eye examination material having a size that is based on the determined size of the monitor;
        provide, to the first computer or the second computer over the network, instructions to display user instructions to provide a user input based on the displayed eye examination material; and
        receive, from the second computer at the server, the user input.

2. The eye examination system of claim 1, wherein the server is further configured to provide, to the first computer over the network, instructions to display a pairing code on the monitor.

3. The eye examination system of claim 2, wherein the server is further configured to receive, from the second computer, information associated with an image of the pairing code captured by a camera of the second computer.

4. The eye examination system of claim 3, wherein the server is further configured to pair the first computer and the second computer.

5. The eye examination system of claim 4, wherein the server is further configured to determine at least one characteristic of a user's vision based on the user input.

6. The eye examination system of claim 5, further comprising an application for the second computer, wherein the application, when run on the second computer is configured to:
    determine a distance between the second computer and the monitor, the distance based on the captured image of the camera calibration pattern.

7. The eye examination system of claim 6, wherein the application, when run on the second computer is configured to:
    display user guidance to move from a current location to the desired location;
    determine that the second computer is at the desired location;
    display a notification that the second computer is at the desired location; and
    provide, to the server over the network, the indication that the second computer is at the desired location.

8. The eye examination system of claim 7, wherein the application, when run on the second computer is configured to track a changing distance between the second computer and the monitor during movement of the second computer from the current location to the desired location.

9. The eye examination system of claim 8, wherein the application is configured to track the changing distance by capturing images of the monitor with the camera of the second computer during the movement.

10. A computer readable data storage medium storing instructions that, when executed by one or more processors, cause the one or more processors to:
    receive, from a server over a network, instructions to display user instructions to capture an image of a calibration pattern that is displayed on a monitor of a computer, using a camera;
    provide, to the server, an indication that the camera is at a desired location; and
    receive, from the server over the network, instructions to display user instructions to provide a user input based on eye exam material that is displayed on the monitor of the computer based on a size of the monitor that has been determined using the image;
    receive the user input; and
    provide, to the server over the network, the user input.

11. The computer readable data storage medium of claim 10, wherein the instructions, when executed by the one or more processors, cause the one or more processors to:
    display user guidance to move the camera from a current location to the desired location.

12. The computer readable data storage medium of claim 11, wherein the instructions, when executed by the one or more processors, cause the one or more processors to:
    determine that the camera is at the desired location.

13. The computer readable data storage medium of claim 12, wherein the instructions, when executed by the one or more processors, cause the one or more processors to:
    display a notification that the camera is at the desired location.

14. The computer readable data storage medium of claim 13, wherein the instructions, when executed by the one or more processors, cause the one or more processors to:
provide, to the server over the network, the indication that the camera is at the desired location.

15. A method, comprising:
providing, from a server to a first computer over a network, instructions to display a resizable box on a monitor of the first computer;
providing, from the server to the first computer over the network, instructions to display user instructions to place a credit card against the monitor in the resizable box and adjust a size of the resizable box to match a size of the credit card;
determining, at the server and based on the size of the resizable box that matches the size of the credit card, a size of the monitor;
providing, from the server to the first computer over the network, instructions to display a pairing code on the monitor;
receiving, at the server from a second computer, information associated with an image of the pairing code captured by a camera of the second computer;
pairing, at the server, the first computer and the second computer;
providing, from the server to the first computer over the network, instructions to display a camera calibration pattern on the monitor, the instructions based on the determined size of the monitor;
providing, from the server to the second computer over the network, instructions to display user instructions to capture an image of the camera calibration pattern;
receiving, from the second computer at the server, an indication that the second computer is at a desired location;
providing, from the server to the First computer over the network and responsive to receiving the indication from the second computer, instructions to display eye examination material having a size that is based on the determined size of the monitor; and
providing, from the server to the first computer or the second computer over the network, instructions to display user instructions to provide a user input based on the displayed eye examination material; and
receiving, from the second computer at the server, the user input.

16. The method of claim 15, further comprising, determining at least one characteristic of a user's vision based on the user input.

17. The method of claim 15, further comprising:
determining, at the second computer, a distance between the second computer and the monitor, the distance based on the captured image of the camera calibration pattern;
displaying, with the second computer, user guidance to move from a current location to the desired location;
determining, with the second computer, that the second computer is at the desired location;
displaying, with the second computer, a notification that the second computer is at the desired location; and
providing, with the second computer to the server over the network, the indication that the second computer is at the desired location.

18. The method of claim 17, further comprising, tracking, with the second computer, a changing distance between the second computer and the monitor during movement of the second computer from the current location to the desired location.

19. The method of claim 18, wherein tracking the changing distance includes capturing images of the monitor with the camera of the second computer during the movement.

20. The method of claim 19, further comprising calibrating, at the second computer, the camera of the second computer based on the image of the camera calibration pattern.

* * * * *